(12) United States Patent
Carpay

(10) Patent No.: US 6,886,409 B2
(45) Date of Patent: *May 3, 2005

(54) SYSTEM FOR CONTROLLING THE FLOW OF A FLUID THROUGH A SUBSTRATE

(75) Inventor: Wilhelmus Marinus Carpay, Liempde (NL)

(73) Assignee: PamGene International B.V., 's-Hertogenbosch (NL)

( * ) Notice: Subject to any disclaimer, the term of this patent is extended or adjusted under 35 U.S.C. 154(b) by 127 days.

This patent is subject to a terminal disclaimer.

(21) Appl. No.: 10/095,834

(22) Filed: Mar. 11, 2002

(65) Prior Publication Data

US 2003/0000311 A1 Jan. 2, 2003

Related U.S. Application Data

(60) Provisional application No. 60/297,592, filed on Jun. 11, 2001.

(30) Foreign Application Priority Data

Mar. 13, 2001 (EP) .............................................. 01200946

(51) Int. Cl.⁷ ............................................. G01L 15/00
(52) U.S. Cl. ................... 73/716; 73/152.18; 73/152.51; 73/195
(58) Field of Search ...................... 73/700–756, 152.18, 73/152.39, 152.42, 152.51, 195, 861.24

(56) References Cited

U.S. PATENT DOCUMENTS

| | | | | |
|---|---|---|---|---|
| 4,072,058 A | * | 2/1978 | Whitehead, Jr. ............. | 73/720 |
| 4,599,906 A | * | 7/1986 | Freud et al. .............. | 73/861.47 |
| 4,782,703 A | * | 11/1988 | Nishi .......................... | 73/708 |
| 5,188,733 A | | 2/1993 | Wang et al. | |
| 5,234,840 A | | 8/1993 | Appleton | |
| 5,352,484 A | * | 10/1994 | Bernard et al. ............. | 427/228 |
| 5,843,767 A | | 12/1998 | Beattie | |
| 6,017,767 A | | 1/2000 | Chandler | |
| 6,168,948 B1 | | 1/2001 | Anderson et al. | |
| 6,197,575 B1 | | 3/2001 | Griffith et al. | |
| 6,383,748 B1 | * | 5/2002 | Carpay et al. .................. | 435/6 |
| 6,422,248 B1 | * | 7/2002 | Furst et al. .............. | 134/22.11 |
| 6,568,282 B1 | * | 5/2003 | Ganzi ...................... | 73/861.42 |

FOREIGN PATENT DOCUMENTS

| | | |
|---|---|---|
| EP | 0 975 427 B1 | 3/2001 |
| WO | WO 87/07954 | 12/1987 |
| WO | WO 95/11755 | 5/1995 |
| WO | WO 97/15394 | 5/1997 |
| WO | WO 98/55852 | 12/1998 |
| WO | WO 01/19517 | 3/2001 |

* cited by examiner

*Primary Examiner*—Edward Lefkowitz
*Assistant Examiner*—Jermaine Jenkins
(74) *Attorney, Agent, or Firm*—Amster, Rothstein & Ebenstein LLP

(57) ABSTRACT

A system is described for controlling the flow of a sample fluid through a substrate having first and second surfaces and at least one area with a plurality of through-going capillary channels. The system comprises a housing having a chamber for receiving the substrate and a pressure differential generator capable of generating and maintaining a pressure difference over the substrate.

23 Claims, 4 Drawing Sheets

SYSTEM FOR CONTROLLING THE FLOW OF A FLUID THROUGH A SUBSTRATE

CROSS-REFERENCE TO RELATED APPLICATIONS

This application claims priority to U.S. Provisional Patent Application Ser. No. 60/297,592, filed Jun. 11, 2001, European Patent Application 01200946.0, filed Mar. 13, 2001, and PCT/EP02/02447, filed Mar. 5, 2002.

BACKGROUND OF THE INVENTION (1) Field of the Invention

The present invention relates to a system for controlling the flow of a fluid, in particular a sample fluid, through a substrate having first and second surfaces and at least one area with a plurality of through-going capillary channels.

(2) Description of the Related Art

A system of this type is described in WO 01/19517. In this system means are provided for applying and/or maintaining a sufficient amount of time a controlled pressure difference. The pressure difference can be regulated by a programmable unit.

SUMMARY OF THE INVENTION

The invention aims to provide an improved system of this type. According to the invention the system comprises a housing having a chamber for receiving the substrate and a pressure differential generator capable of generating and maintaining a pressure difference over the substrate. The invention will be further explained by reference to the drawings showing an embodiment of the system of the invention.

BRIEF DESCRIPTION OF THE SEVERAL VIEWS OF THE DRAWINGS

FIG. 1 schematically shows an embodiment of the system of the invention.

FIG. 2 shows a cross-section of the housing of the system of FIG. 1, wherein a substrate is accommodated in the housing.

FIG. 3 shows a perspective view of an example of the substrate shown in cross-section in FIG. 2.

FIG. 4 shows a cross-section of the housing of FIG. 2, wherein a washing device is placed on the housing.

DETAILED DESCRIPTION OF THE INVENTION

Referring to FIG. 1, there is shown a system for controlling the flow of a sample fluid through a substrate 1 which is shown in a perspective view by way of example in FIG. 3. In this embodiment the substrate 1 is made as a laminated array-membrane comprising upper and lower outer layers 2 and an intermediate strip of aluminium oxide. The outer layers 2 are provided with four openings 3, the openings 3 of the upper and lower layers 2 being aligned. In this manner the strip of aluminium oxide is exposed at four areas or wells 4. The strip of aluminium oxide comprises a large number of through-going capillary channels oriented mainly perpendicular to the upper and lower surfaces of the strip. The capillary pressure of the channels is very high. In a practical embodiment of the substrate 1, the channels in the strip of aluminium oxide may have a spacing of approximately 150–200 nm, wherein a binding substance is bound to the substrate in groups of channels at a spacing of 200 mm. A group of channels can be indicated as a dot or dot area. Each area 4 of the substrate 1 may have approximately 400 dots. For a further description of the substrate reference is made to the above-mentioned international patent application PCT/US00/24885. It will be understood that the number of exposed areas of the substrate, the number of dots and the dimensions are mentioned by way of example only and may be varied as desired.

The system shown in FIGS. 1 and 2 comprises a housing 5 having an upper housing part 6 and a lower housing part 7. The upper and lower housing parts 6, 7 determine a chamber 8 for receiving the substrate 1. As shown in FIG. 2, the substrate 1 is received in the chamber 8 together with a holding device 9 which includes an upper and lower structure 10 and 11, respectively. Both upper and lower structures 10, 11 are provided with four cylindrical extensions 12 mainly aligned with the areas 4 of the substrate 1. The holding device 9 is made of a plastic material. The device 9 is further described in a co-pending patent application "Device for holding a substrate" of the same applicant, European Patent Application 01200946.0, filed Mar. 13, 2001.

The chamber 8 comprises cylindrical chamber sections 13 in the upper and lower housing parts 6, 7, in which the cylindrical extensions 12 are received. In the upper housing part 6, these cylindrical chamber sections 13 are interconnected by a channel 14 providing a connection between the cylindrical chamber sections 13 and the environment of the housing 5, so that an ambient pressure reference is available in these upper cylindrical chamber sections 13.

In the lower housing part 7, the cylindrical chamber sections 13 are also interconnected by a channel 15. In this case the channel 15 is connected to a means for generating a pressure difference over the substrate 1. In the embodiment shown the means for generating a pressure difference over the substrate 1 is made as means to change the volume of the chamber 8, in this case the part of the chamber 8 under the substrate 1. More particularly, the means for generating a pressure difference are implemented as a cylinder piston assembly 16 schematically shown in FIG. 1.

In FIG. 2, a sample fluid 17 is schematically shown in two cylindrical extensions 12 of the device 9, so that only at the corresponding areas 4 of the substrate 1 the sample fluid can be passed through the capillary channels of the substrate 1. As schematically indicated by means of sealing rings 18, two cylindrical chamber sections 13 are sealed with respect to the channel 15 so that a pressure difference over the substrate 1 is only generated at the areas 4 where a sample fluid 17 is present.

During transporting the sample fluid 17 through the capillary channels of the substrate 1, substances in the sample fluid can be bound by the binding substance in these capillary channels. In order to allow a mutual comparison of test results, it is important to accurately control the time period for transporting the sample fluid through these capillary channels. In order to control this transport time in an accurate manner, the system shown in FIG. 1 is provided with means 19 for maintaining the pressure difference over the substrate at a controlled level during the transport of the sample fluid 17 through the capillary channels. Generally, said means 19 will be implemented in a programmable processing unit. Preferably the pressure difference is maintained at a constant level during the transport of the sample fluid. In order to determine the time period during which the sample fluid 17 is transported through the capillary channels of the substrate 1, the processing unit 19 comprises means for setting a desired pressure difference.

Figure 1:
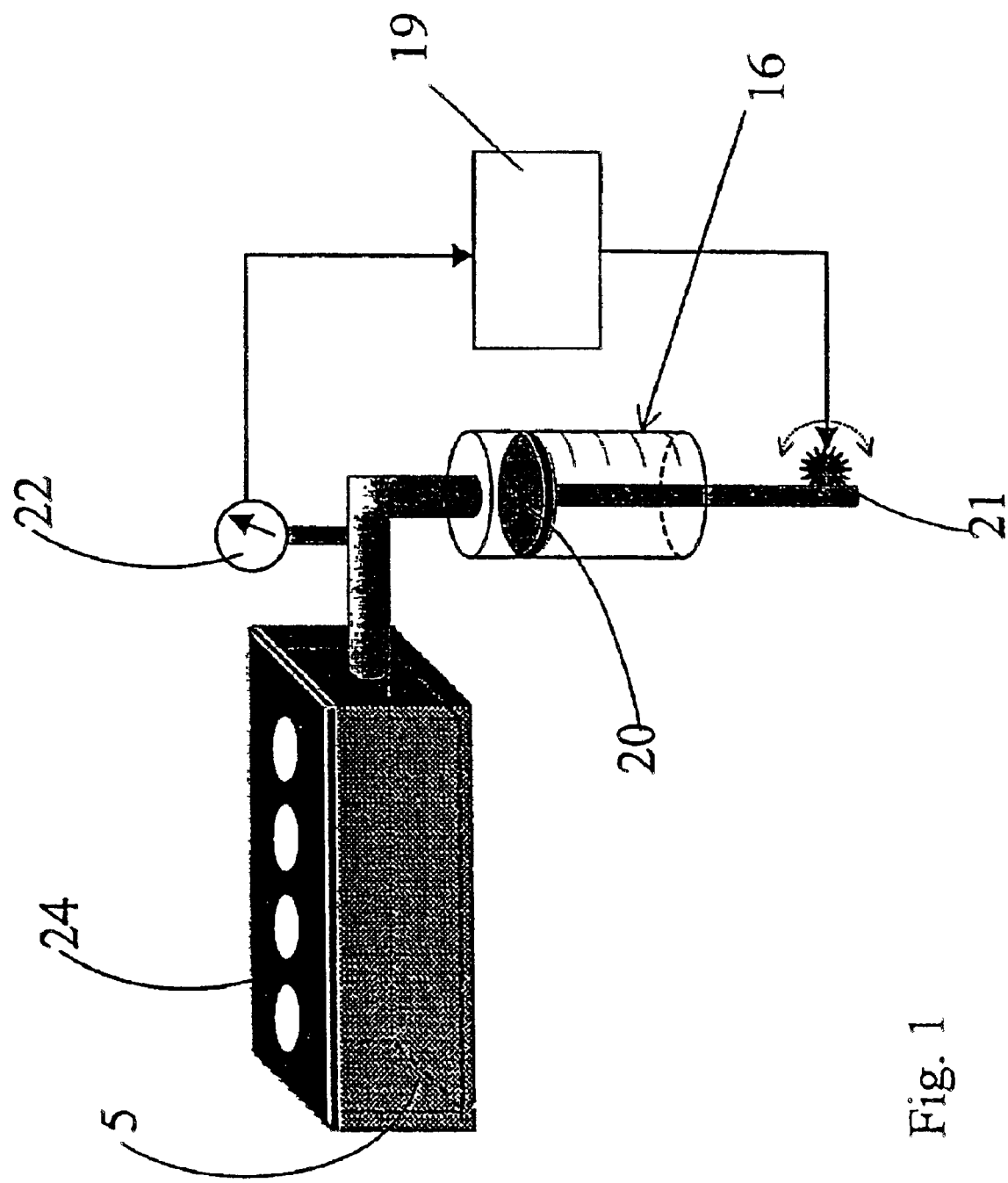
Figure 2:
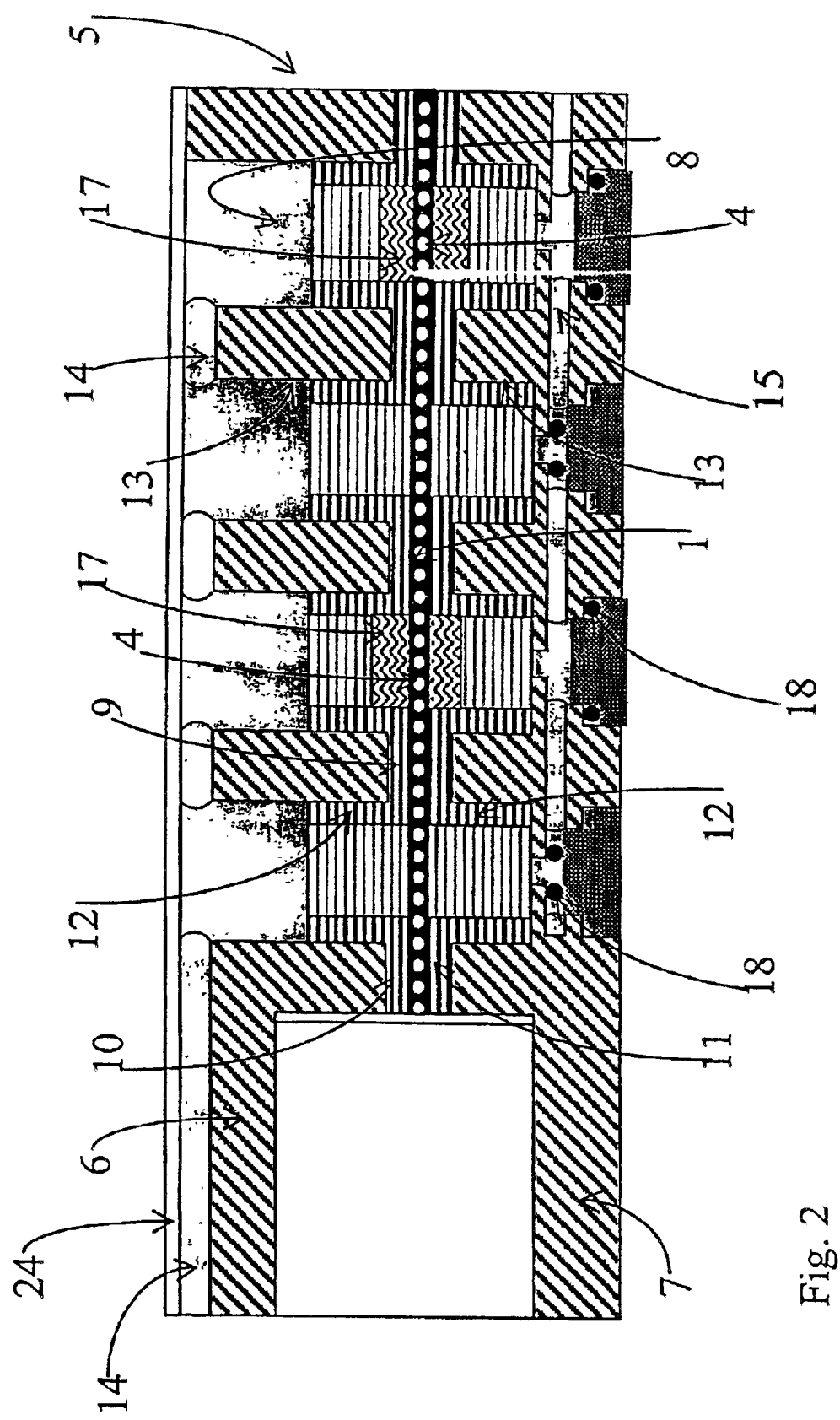
Figure 3:
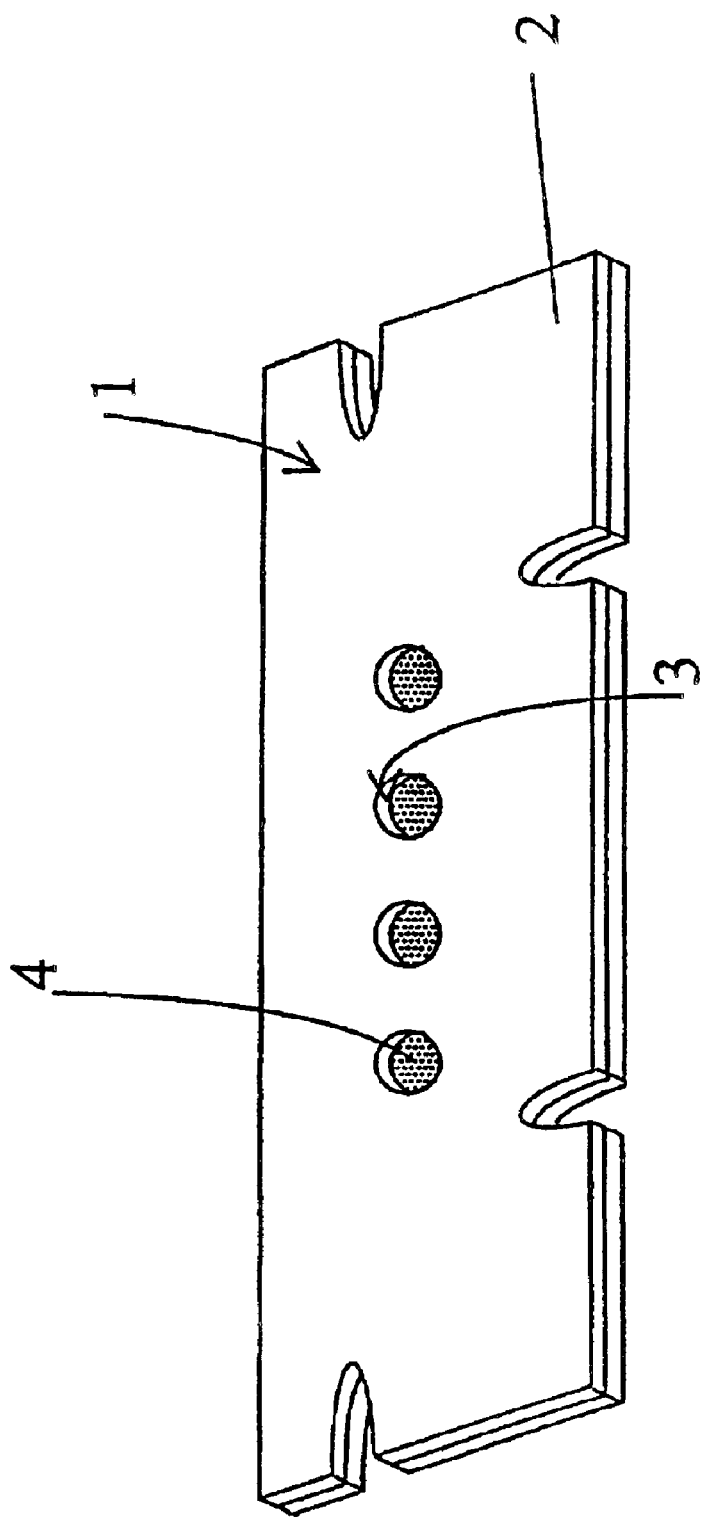

As mentioned, the means for generating a pressure difference over the substrate to transport the sample fluid 17 from the upper surface of the substrate 1 to the lower surface is implemented as a cylinder piston assembly 16 having a piston 20 which is moveable by means of a schematically indicated actuator 21. This actuator 21 or control device is controlled by the processing unit 19 in dependence on the pressure in the chamber 8 as measured by means of a schematically indicated pressure measuring device 22. Assuming that at the beginning of an assay the sample fluid 17 is located in the upper cylindrical extensions 12, the processing unit 19 starts to generate a pressure difference over the substrate 1 by generating in the chamber 8 under the substrate 1 a pressure lower than the ambient pressure. This pressure difference transports the sample fluid 17 through the capillary channels of the substrate 1 so that the sample fluid 17 will gradually be transported towards the lower cylindrical extensions 12 of the lower structure 11. This would result in an increase of the pressure in the chamber 8 under the substrate 1 and this pressure increase is measured by the measuring device 22. In view of this pressure increase as measured by the processing unit 19, the processing unit 19 operates the actuator 21 to displace the piston 20 to maintain the pressure difference at a constant level. In this manner the sample fluid 17 is transported through the capillary channels of the substrate 1 in an accurately determined time period.

Generally the sample fluid 17 should be transported through the capillary channels of the substrate 1 a number of times in order to allow for a sufficient binding action of the binding substance in the capillary channels of the substrate 1. In order to reduce the overall time of the assay, it is important to reduce the time required for reversing the transport of the sample fluid through the capillary channels. In the system described, the time for reversing the transport is reduced by monitoring the operation of the processing unit 19 for maintaining the pressure difference at a constant level. As soon as the processing unit stops to operate the actuator 21 for maintaining the pressure difference at a constant level, the pressure difference over the substrate is changed immediately in such a manner that the sample fluid 17 is transported in the reverse direction from the lower surface of the substrate 1 towards the upper surface through the capillary channels. For, as soon as the pressure difference remains constant without any displacement of the piston 20, this is an indication that the sample fluid 17 is completely transported through the capillary channels of the substrate 1. To change the pressure difference, the piston 20 is displaced in the opposite direction by the actuator 21. Thereby, the sample fluid 17 is transported towards the upper surface of the substrate 1. Thereby the pressure in the chamber 8 under the substrate 1 would decrease and this is measured by the measuring device 22. The processing unit 19 operates the actuator 21 to displace the piston 20 to maintain the pressure difference at a constant level. In this manner the sample fluid 17 can be transported in opposite directions through the capillary channels of the substrate 1 in a minimum time period.

It is noted that the pressure difference required to transport the sample fluid 17 through the capillary channels of the substrate 1 is much lower than the capillary pressure of the capillary channels of the substrate 1. In this manner it is prevented that the sample fluid 17 is pushed off the upper or lower surface of the substrate 1 when the sample fluid is completely transported through the channels.

In the system described, the processing unit 19 is adapted to measure the change of volume required to transport the sample fluid 17 completely through the capillary channels from the upper to the lower surface and vice versa. The change of volume can be measured for example by measuring the displacement of the piston 20. This change of volume should be constant for each transport step of the system, i.e. each time the sample fluid 17 is transported from the upper to the lower surface or vice versa. If the change of volume required to completely transport the sample fluid varies, this is an indication that a leak is present somewhere in the system so that the system should be checked by an operator. The processing unit 19 can provide a warning indication to signal an operator a variation in the change of volume.

Further, the processing unit 19 can measure the change of volume required to transport the sample fluid completely through the capillary channels of the substrate 1 in order to compare this change of volume with the initial volume of the sample fluid 17 provided in the cylindrical extensions 12. This initial volume can be provided as an input to the processing unit 19. As an alternative, the processing unit 19 could also be used to automatically provide a predetermined initial volume in the cylindrical extensions 12 for performing an assay. If a difference between the initial volume and the required change of volume is measured, this is also an indication of a leak in the system. This difference can be indicated by the processing unit 19 to warn an operator.

A further advantage of the system described is that the processing unit 19 can measure the time to transport the sample fluid through the capillary channels of the substrate 1, i.e. the flow rate. If this time or flow rate varies this is an indication that an air bubble or a contamination is blocking at least a part of the capillary channels. As the flow resistance of the substrate and the pressure used to transport the fluid are known or can be established, the processing unit 19 can determine the flow rate and/or the time required to transport an amount of the sample fluid through the substrate. Any deviation from the expected time or flow rate can be used as an indication of an error situation.

Figure 4:
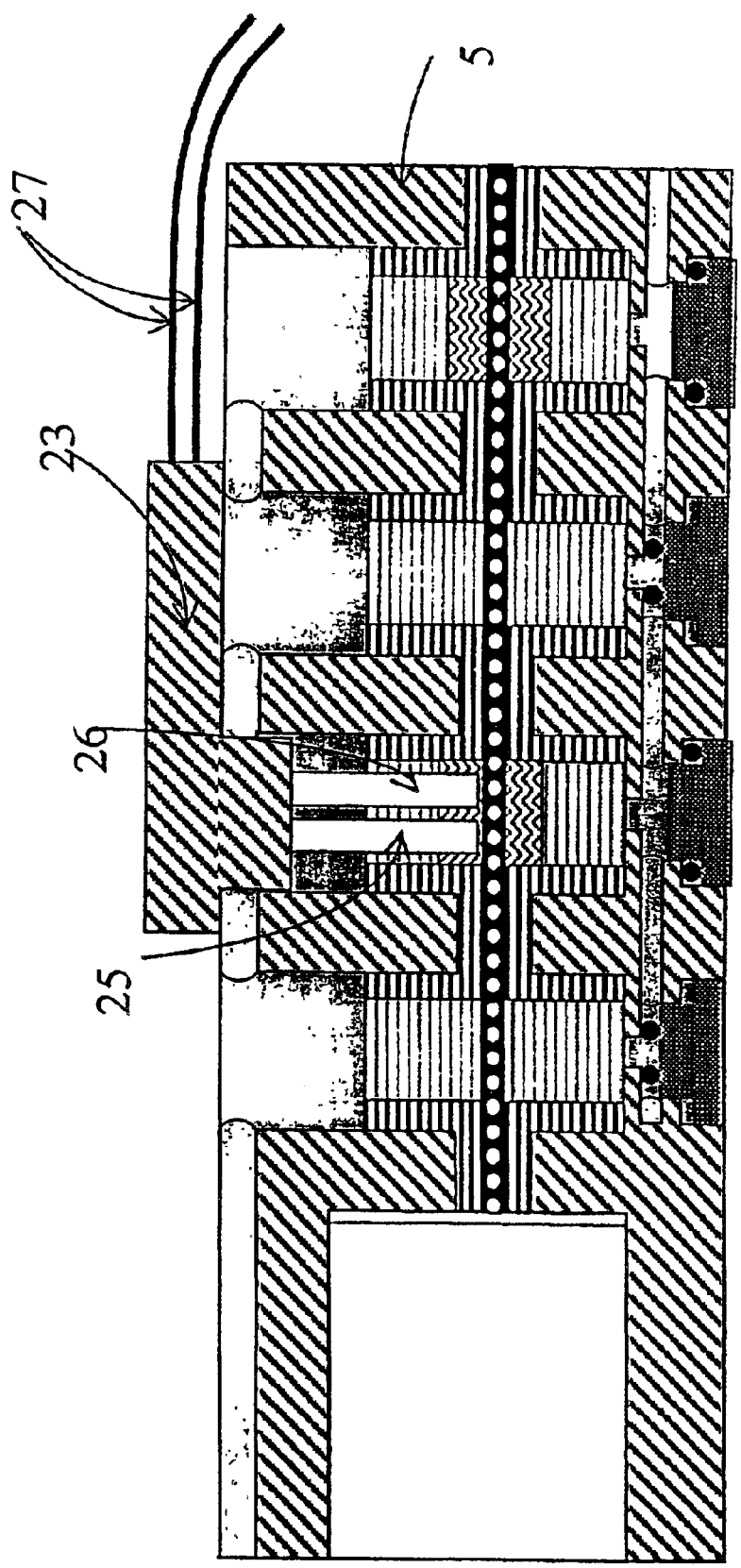

The system described shows the advantage that a washing operation to clean the capillary channels of the substrate 1 can be carried out in an easy manner. According to FIG. 4 a washing device 23 is placed on top of the housing 5 after removal of an upper glass cover 24 normally located on top of the housing 5. The glass cover allows a direct vision on to the upper surface of substrate areas 4 during transport of the sample fluid 7 through the channels. The washing device 23 is provided with washing fluid feed and discharge tubes 25 and 26. Washing is performed in a programmable manner. For example, a washing fluid can be can be fed on top of the substrate 1, the washing fluid can be transported through the capillary channels of the substrate 1 a number of times and the washing fluid can be discharged. Discharging of the washing fluid may occur for example in a continuous flow at a slightly higher rate than feeding. If the processing unit 19 generates a positive pressure under the substrate 1 the washing fluid will stay on top of the substrate 1. By generating a negative pressure under the substrate 1, the washing fluid is transported through the capillary channels of the substrate 1 to the lower side in the same manner as described for a sample fluid. By reversing the pressure difference the washing fluid is transported back to the upper side of the substrate 1 again. In this manner the capillary channels of the substrate can be cleaned in an efficient manner. Contamination of the channel 15 is prevented as the washing fluid will not be pushed off of the lower side of the substrate 1. The washing device is connected to a source of washing fluid not shown by means of schematically indicated tubes 27. The washing operation is controlled by the processing unit 19.

Other embodiments within the scope of the claims herein will be apparent to one skilled in the art from consideration of the specification or practice of the invention as disclosed herein. It is intended that the specification be considered exemplary only, with the scope and spirit of the invention being indicated by the following claims.

In view of the above, it will be seen that the several advantages of the invention are achieved and other advantages attained.

As various changes could be made in the above methods and compositions without departing from the scope of the invention, it is intended that all matter contained in the above description and shown in the accompanying drawings shall be interpreted as illustrative and not in a limiting sense.

All references cited in this specification are hereby incorporated by reference. The discussion of the references herein is intended merely to summarize the assertions made by the authors and no admission is made that any reference constitutes prior art. Applicants reserve the right to challenge the accuracy and pertinence of the cited references.

What is claimed is:

1. A system for controlling the flow of a fluid through a substrate having first and second surface and at least one area with a plurality of through-going capillary channels, characterized by a housing having a chamber for receiving the substrate, means for generating a pressure difference over the substrate to transport the fluid from the first to the second surface and vice versa through the channels of said at least one area, and means for maintaining the pressure difference at a controlled level during the transport of the fluid through the channels.

2. The system of claim 1, wherein the fluid is a sample fluid.

3. The system of claim 1, wherein the maintaining means comprises means for setting a desired level of the pressure difference.

4. The system of claim 3, wherein the means for generating a pressure difference comprise means to change the volume of the chamber, wherein the maintaining means comprises a pressure measuring device and a control device to operate the volume changing means.

5. The system if claim 3, comprising means for monitoring the operation of the maintaining means, wherein said monitoring means are adapted to change the pressure difference over the substrate to transport the fluid in the reverse direction through the channels as soon as the operation of the maintaining means shows that the fluid has been transported through the substrate.

6. The system of claim 1, wherein the means for generating a pressure difference comprise means to change the volume of the chamber, wherein the maintaining means comprises a pressure measuring device and a control device to operate the volume changing means.

7. The system of claim 6, wherein the monitoring means monitor the operation of said maintaining means, wherein the pressure difference is changed to transport the fluid in reverse direction as soon as the pressure difference remains at a constant level without operation of the maintaining means.

8. The system of claim 6, wherein the volume changing means comprises a cylinder piston assembly connected to the chamber and wherein said control device operates the piston of the cylinder piston assembly.

9. The system of claim 6, wherein the pressure difference is changed in the reverse direction by reversing the change of volume.

10. The system of claim 6, further comprising means for measuring the change of volume required to transport the fluid through the channels from the first to the second surface or vice versa, wherein said measuring means is adapted to indicate if said change of volume is varying in successive transports of the fluid through the channels.

11. The system of claim 10, comprising means to input the initial volume of a sample fluid, wherein said measuring means is adapted to compare said initial volume and said change of volume, wherein said measuring means provides an indication if a difference is established.

12. The system of claim 6, comprising means for measuring the time required to transport the fluid through the channels from the first to the second surface or vice versa, wherein said measuring means is adapted to indicate if the measured time indicates a variation of fluid flow rate.

13. The system of claim 6, comprising a washing device having washing fluid feed and discharge tubes wherein the washing device is adapted to supply and remove washing fluid to and from the chamber as controlled by the maintaining means.

14. The system if claim 1, comprising means for monitoring the operation of the maintaining means, wherein said monitoring means are adapted to change the pressure difference over the substrate to transport the fluid in the reverse direction through the channels as soon as the operation of the maintaining means shows that the fluid has been transported through the substrate.

15. The system of claim 14, wherein the monitoring means monitor the operation of said maintaining means, wherein the pressure difference is changed to transport the fluid in reverse direction as soon as the pressure difference remains at a constant level without operation of the maintaining means.

16. The system of claim 14, wherein the monitoring means comprises a cylinder piston assembly connected to the chamber and wherein said monitoring means operates the piston of the cylinder piston assembly.

17. The system of claim 14, wherein the pressure difference is changed in the reverse direction by reversing the change of volume.

18. The system of claim 14, further comprising means for measuring the change of volume required to transport the fluid through the channels from the first to the second surface or vice versa, wherein said measuring means is adapted to indicate if said change of volume is varying in successive transports of the fluid through the channels.

19. The system of claim 14, comprising means for measuring the time required to transport the fluid through the channels from the first to the second surface or vice versa, wherein said measuring means is adapted to indicate if the measured time indicates a variation of fluid flow rate.

20. The system of claim 14, comprising a washing device having washing fluid feed and discharge tubes wherein the washing device is adapted to supply and remove washing fluid to and from the chamber as controlled by the maintaining means.

21. The system of claim 1, wherein a binding substance is bound to the substrate.

22. The system of claim 1, wherein the substrate is an electrochemically manufactured metal oxide membrane.

23. The system of claim 22, wherein the metal oxide membrane is an aluminum oxide membrane.

* * * * *

UNITED STATES PATENT AND TRADEMARK OFFICE
CERTIFICATE OF CORRECTION

PATENT NO. : 6,886,409 B2
APPLICATION NO. : 10/095834
DATED : May 3, 2005
INVENTOR(S) : Wilhelmus Marinus Carpay It is certified that error appears in the above-identified patent and that said Letters Patent is hereby corrected as shown below:

Title page

Item (73), Assignee, "PamGene International B.V." should read --PamGene B.V.--.

Signed and Sealed this

Nineteenth Day of June, 2007

JON W. DUDAS
*Director of the United States Patent and Trademark Office*